United States Patent [19]
Sullivan et al.

[11] Patent Number: 5,147,375
[45] Date of Patent: Sep. 15, 1992

[54] SAFETY FINGER PRICK INSTRUMENT

[76] Inventors: Ann Sullivan, 5605 N. Winthrop Ave., Indianapolis, Ind. 46220; Lara Engelking; Scott T. Engelking, both of 7256 Jessman Rd. E. Dr. #H, Indianapolis, Ind. 46256

[21] Appl. No.: 708,759

[22] Filed: May 31, 1991

[51] Int. Cl.⁵ .............................. A61B 17/34
[52] U.S. Cl. .................................... 606/182
[58] Field of Search ................... 606/181–184; 604/240, 241

[56] References Cited
U.S. PATENT DOCUMENTS

| | | | |
|---|---|---|---|
| Re. 32,922 | 5/1989 | Levin et al. | 606/182 |
| 2,604,890 | 7/1952 | Burnside | 604/241 |
| 4,139,011 | 2/1979 | Beroit et al. | 606/182 |
| 4,203,446 | 5/1980 | Hofert et al. | 606/182 |
| 4,379,456 | 4/1983 | Cornell et al. | 606/182 |
| 4,416,279 | 11/1983 | Lindner et al. | 606/182 |
| 4,469,110 | 9/1984 | Slama | 606/182 |
| 4,817,603 | 4/1989 | Turner et al. | 606/182 |

*Primary Examiner*—Max Hindenburg
*Attorney, Agent, or Firm*—Robert A. Spray

[57] ABSTRACT

An extremely safe skin-pricker device in the form of an open-ended tubular shell which carries an open-coil actuator spring which when released by a latchable trigger pushes an actuator shaft to move and cause the pricker needle to travel not only to an intermediate position of relieved stress but also to travel the short distance for the pricking procedure, but then, by the spring's over-travel movement permitted by its open-coil nature, the spring pulls on the shaft to withdraw the needle safely inwardly of a cover-cap which during the pricking is retained on the open end of the shell.

4 Claims, 2 Drawing Sheets

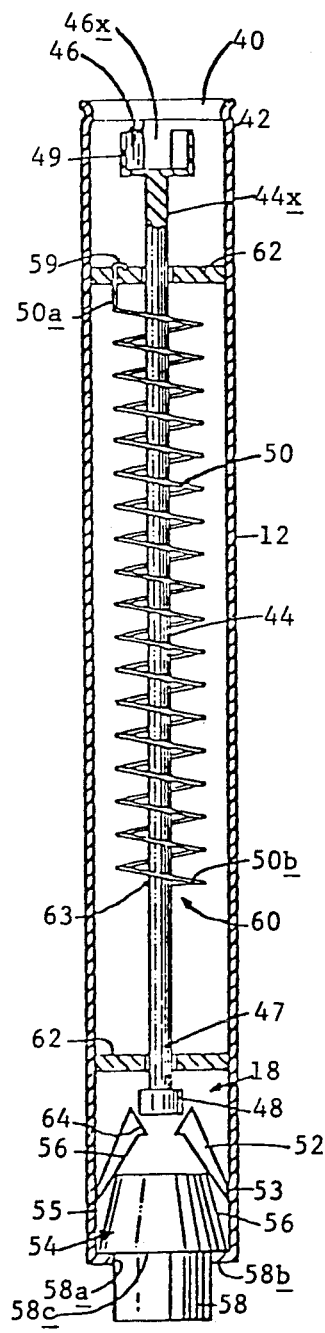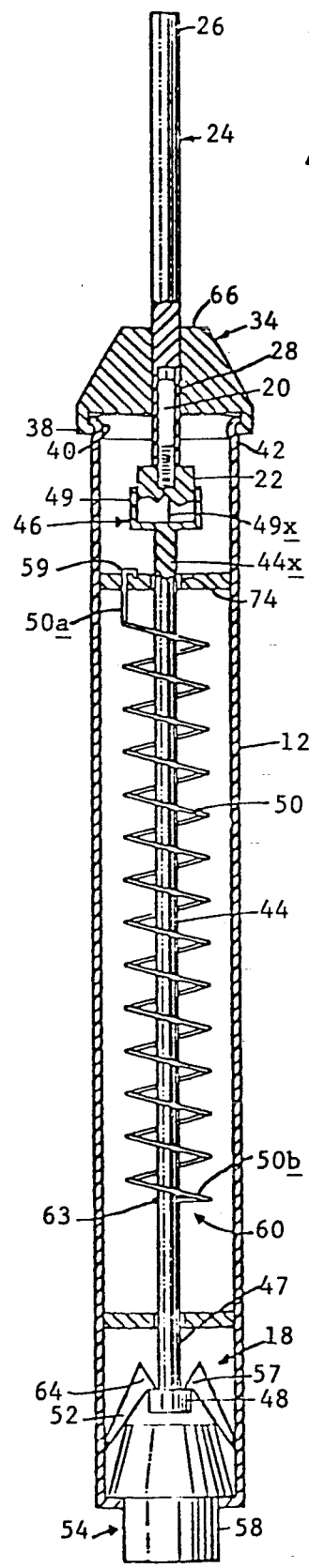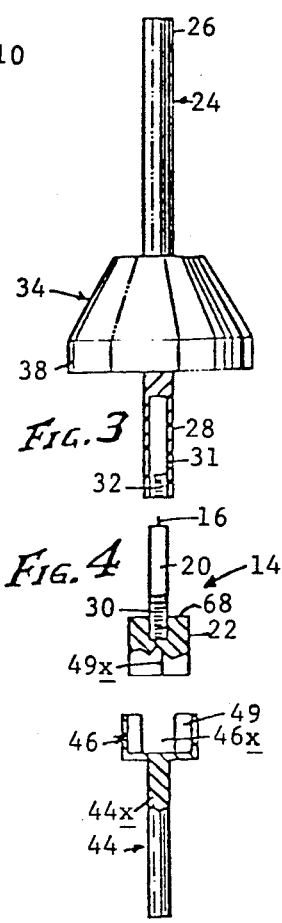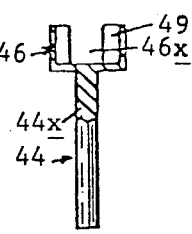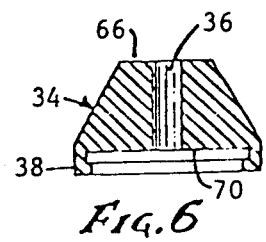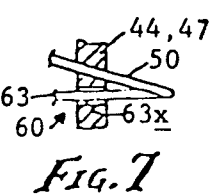

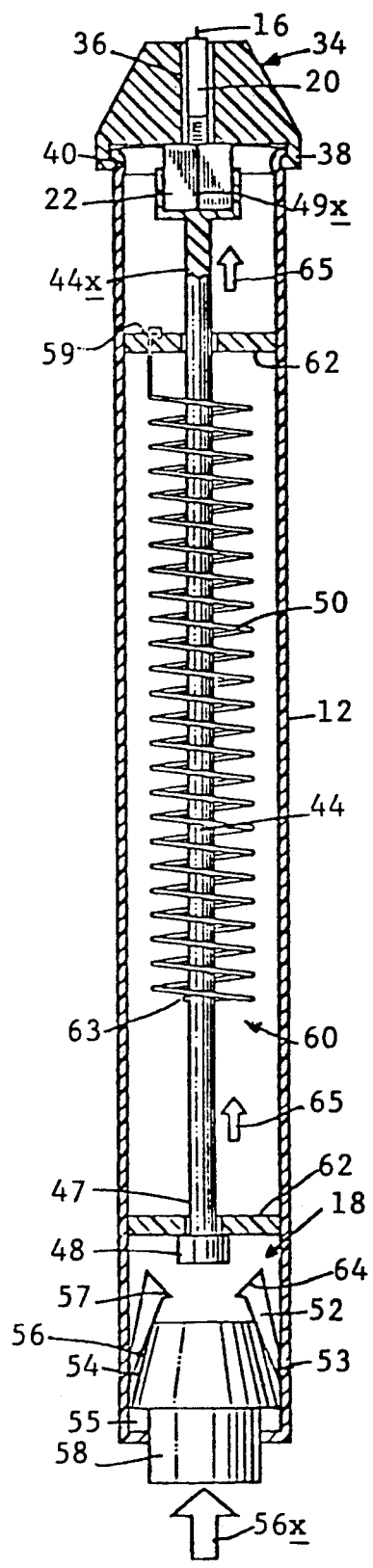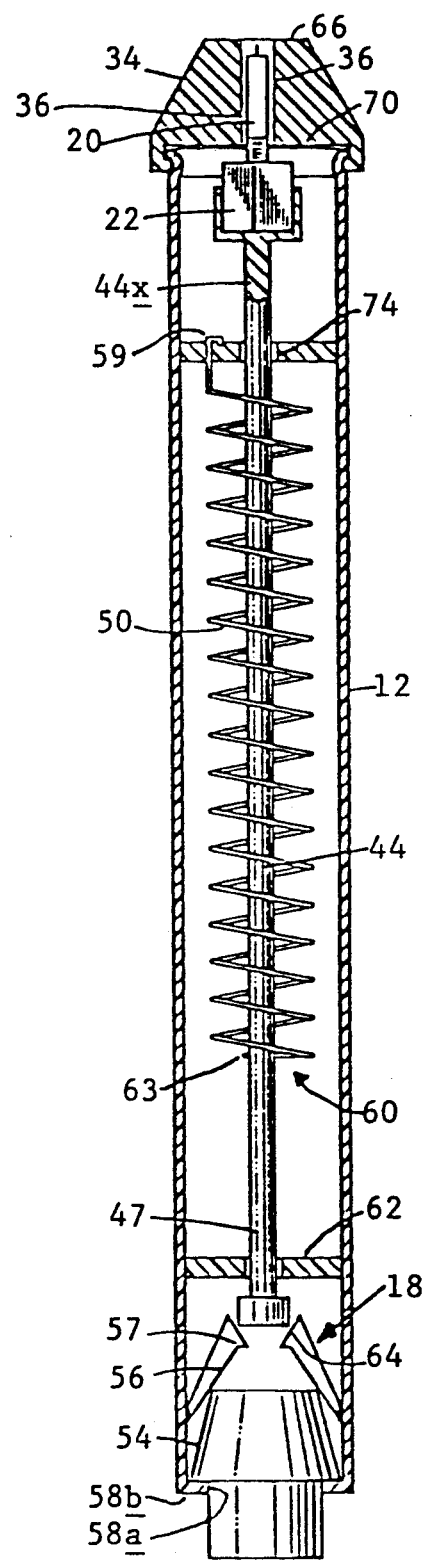
FIG. 8
FIG. 9

SAFETY FINGER PRICK INSTRUMENT

FIELD AND BRIEF BACKGROUND OF THE INVENTION AND ITS GREAT NEED

The present invention relates to a device for protection from infections being accidentally transmitted from one person to another, particularly from an infected person to medical personnel who have to be in touching engagement with an infected person.

More particularly, the present invention relates to and achieves a novel and advantageous device by which medical technicians can easily avoid any change of getting on the technician's person any blood from the person from whom the technician is going to extract a blood specimen in a "skin pricking" procedure.

For several years, much of the public and surely most all persons in the entire medical field have been increasingly aware of the great and often tragic danger of infection to medical personnel being caused by accidental contamination from an infected person's body fluids.

And skin-pricking procedures are necessarily done surely millions of times per year, such as in a preliminary step of blood-drawing from blood donors, and for surgery candidates, etc.

Nevertheless no prior art known by the present inventors provides the present concepts for a skin-pricking device which is comparable to the present invention which achieves an inexpensive, easily learned, and practically foolproof device for safely drawing blood in a skin-pricking procedure.

SUMMARY OF THE INVENTION CONCEPTS SHOWN IN THE ILLUSTRATIVE EMBODIMENT

An extremely safe skin-pricker device in the form of an open-ended tubular shell which carries an open-coil actuator spring which when released by a latchable trigger pushes an actuator shaft to move and cause the pricker needle to travel not only to an intermediate position of relieved stress but also to travel the short distance for the pricking procedure, but then, by the spring's over-travel movement permitted by its open-coil nature, the spring pulls on the shaft to withdraw the needle safely inwardly of a cover-cap which during the pricking is retained on the open end of the shell.

The device is of single-use nature as to its pricker needle and other components of an expendible assembly, including that cover-cap, a sheath, and the needle subassembly of the needle, a needle stem, and a needle base.

The sheath, having a freely-slidable fit in a hole in the cap, provides the plural functions of being a handle for the expendible assembly, and, by its threaded connection with the needle base, the sheath functions also to both deposit the needle subassembly in a receiver cup on the actuator shaft, but also to serve as a safe retriever for the needle and the needle subassembly after the skin-pricking has been done; and thus all components which have been exposed to the needle or the patient's finger are discarded safely, while the shell, spring, and actuator shaft and its trigger body remain, still fully clean, for the next procedure with a new needle assembly, for there is no way to re-latch the actuator shaft except by the sheath provided with the kit for the next procedure.

PRIOR ART CONTRASTED

A contrast to the prior art shows particulars of both the significant differences from, and the significant advantages of the present invention over the prior art.

Accordingly, comparison and contrast is here shown as to what the present inventors believe to be the least remote of any prior art of their awareness, i.e., a "Soft Touch" device distributed by Boehringer Mannheim, a well-known manufacturer of medical devices. Then, Section 2 of this prior art discussion shows similarly the contrast of the present invention over the only reference cited by the Patent Office, i.e., U.S. Pat. No. 4,379,456, of Cornell, issued Apr. 12, 1983.

1. POTENTIAL FOR CONTAMINATION AS TO THE "SOFT TOUCH3[ PRODUCT DESCRIBED ABOVE

1.A Removal of Lancet Cover

The Soft Touch lancet cover is a small pea-like plastic sheath. The sheath's size, difficult manipulation and close proximity to the needle tip increases the risk for contamination of the sterile needle tip during sheath removal.

In contrast, the present invention provides a safety needle cover which is an easily manipulated and elongated plastic sheath. Due to the enclosed proximity of the needle upon removal of the sheath, the potential for contamination of the sterile needle is eliminated.

1.B. Replacement of Device Tip

Due to the two piece construction of the Soft Touch device, there is an added potential for contamination of the sterile needle while replacing the device tip. (Contamination could be due to needle contact with technician's finger, the device tip or any other factor in the environment while attempting to position the device tip.)

In contrast, due to the single-piece construction of the device of the present invention, the potential for contamination is eliminated. Contact with the technician or environment is eliminated by the needle's complete enclosure within the device's barrel.

1.C. Replacement of Lancet Cover and Removal of Lancet

The Soft Touch manufacturer suggests recapping the exposed contaminated needle with the small pea-like lancet cover. This procedure requires pinpoint accuracy and, therefore, renders a high risk for needle puncture to the technician. The manufacturer suggests in the instruction booklet that the lancet cover may come off which, in turn, creates a greater risk for accidental needle stick.

In contrast, the present invention provides a completely enclosed recapping system which eliminates any risk of contaminated needle puncture to the technician. Because institutional policy dictates no recapping of exposed contaminated needles, technicians using the Soft Touch device probably most often attempt to remove the lancet while exposed. This poses an equivalent level of potential exposure to the technician.

In contrast, due to the fully enclosed design of the present invention's device, there are no exposed contaminated parts; thus, removal of the contaminated needle poses no risk of exposure to the technician.

1D. Accidental Re-Cock and Trigger of Device

During unloading of the exposed contaminated needle the Soft Touch device can easily be accidentally re-cocked due to its sliding feature. The trigger button, centrally located on the side of the sliding barrel, creates a high potential for accidental re-firing of the contaminated needle and subsequent body fluid transmission from patient to technician.

In contrast, the present invention provides that all methods of engaging the device require the use of the protective sheath. This device may only be engaged with the needle assembly in an intentional manner.

1.E. Lengthy Exposure of Contaminated Needle due to Multiple Steps to Unload Device The multiple steps to unload the Soft Touch device leave the contaminated needle exposed for a variable amount of time.

In contrast, the present invention provides that its needle is never exposed during unloading, due to the enclosed nature concepts.

1F. Contaminated Lancet Disposal

Using institutional policy for uncapped needle disposal, the technician using a Soft Touch device must handle the exposed needle for an undetermined amount of time prior to disposal in a proper receptacle.

In contrast, the present invention provides that the needle cannot be removed in an exposed state.

When using the Soft Touch manufacturer's recommended procedure for contaminated needle disposal, the instability of the lancet cover during disposal renders it dangerous.

In contrast, the present invention provides a stable interlocking thread connection between the sheath and needle base; and thus safe disposal of the contaminated needle is facilitated.

Now is shown the present invention as contrasted to the only reference cited and initially applied by the Patent Office, Cornell, U.S. Pat. No. 4,379,456:

A contrast to the prior art shows particulars of both the significant differences from, and the significant advantages of the present invention over the prior art, Cornell, as cited by the Examiner.

2.A. Removal of Cornell Lancet Cover

The Cornell lancet cover is a small pea-like plastic sheath. The sheath's size, difficult manipulation and close proximity to the needle tip increases the risk for contamination of the sterile needle tip during sheath removal.

In contrast, the present invention provides a safety needle cover which is an easily manipulated and elongated plastic sheath. Due to the enclosed proximity of the needle upon removal of the sheath, the potential for contamination of the sterile needle is eliminated.

2.B. Replacement of Lancet Cover and Removal of Lancet

With the Cornell device, recapping the exposed contaminated needle with the small pea-like lancet cover is very difficult. This procedure requires pinpoint accuracy and, therefore, renders a high risk for needle puncture to the technician. Due to the unstable relationship between the cap and the contaminated needle of Cornell's device, the lancet cover may easily come off which in turn creates a greater risk for accidental needle stick.

In contrast, the present invention provides a completely enclosed recapping system which eliminates any risk of contaminated needle puncture to the technician. In addition, due to the threaded connection between the sheath and contaminated needle of the present invention, the risk of an accidental needle stick is further eliminated. Because institutional policy dictates no recapping of exposed contaminated needles, technicians using the Cornell device probably most often attempt to remove the lancet while exposed. This poses an equivalent level of potential exposure to the technician.

In contrast, due to the fully enclosed design of the present invention's device, there are no exposed contaminated parts; thus, removal of the contaminated needle poses no risk of exposure to the technician.

2.C. Accidental Re-Cock and Trigger of Device

In the Cornell device, the same lever is used to perform three critical functions; cocking, firing and unloading. Due to this construction there is a great possibility that a contaminated needle may be recocked during the unloading procedure. This creates a potential danger for accidental re-firing of the contaminated needle and subsequent body fluid transmission from patient to technician.

In contrast, the present invention provides that all methods of engaging the device require the use of the protective sheath. This device may only be engaged with the needle assembly in an intentional manner.

2.D. Contaminated Cap Disposal

Following the skin pricking procedure the contaminated cap body must be discarded.

When using the Cornell device the technician must have direct contact with the contaminated cap for disposal.

In contrast, due to the construction of the needle assembly for the present invention there is no direct contact by the technician with any contaminated parts.

BRIEF DESCRIPTION OF THE FIGURES OF DRAWINGS

FIGS. 1, 2, 8 and 9 are longitudinal cross-sectional views of a device of the present invention, and more particularly:

FIG. 1 shows the parts at an at-rest position, prior to the attachment of the needle assembly;

FIG. 2 is an overall view of the device of FIG. 1, but now having the needle assembly inserted to the shell, and with the parts in a latched condition;

FIGS. 3 and 4 are detail views, respectively showing:

FIG. 3 shows the cover sheath and the slidable disk-cap mounted on it;

FIG. 4 is a needle assembly;

FIG. 5 is a fragmental detail of the end of the control shaft which receives the needle assembly;

FIG. 6 is a transverse cross-sectional view of the disk-cap;

FIG. 7 is a fragmental detail view illustrating a connection of an actuator spring to the control shaft; and FIGS. 8 and 9 are sequential views, respectively illustrating the device during the skin-pricking procedure, and after the skin-pricking procedure.

COMPONENTS IN NUMERICAL LISTING

For convenience of reference, although for many features the description could be considered as oversimplified for the sake of brevity, the various components are here listed as to the illustrative embodiment:
10—device's "permanent" parts
12—outer shell
14—needle assembly
16—needle
18—latch and actuator
20—needle stem
22—needle base
24—sheath
26—sheath closed end
28—sheath open end
30—needle stem threads (male)
31—inner wall of 24
32—sheath threads (female)
34—disk
36—disk hole
38—disk wall's inturned lip
40—recess for 38, in 42 of 12
42—top end of 12
44—control rod
44x—outer end of 44
46—control rod cup
46x—slots in cup 46
47—inner end of 44
48—control rod latch lug
49—cup 46's open end wall
49x—corners of needle base 22
50—spring
50a.—upper end of spring 50
50b.—lower end of spring 50
52—latching fingers
53—connection of 52 to 12
54—trigger
55—inner end wall of 12
56—slant of 52/54
56x—Firing push
57—latch surface of 52
58—trigger's outer head
58a—hole in wall 58b
58b—transverse wall of 12
58c—shoulder on trigger 54
59—connection of spring 50 to 12/62
60—connection of spring 50 to 44
62—support disks for 44
63—end of the spring 50
63x—hole through which spring 50 passes
64—cam walls of 52 forced by lug 48
65—arrows (movement)
66—outer wall of disk 34
68—outer wall of needle-base 22
70—inner wall of disk 34
74—hole in support disks 62

DETAILED DESCRIPTION OF THE ILLUSTRATIVE EMBODIMENT SHOWN IN THE DRAWINGS

As shown in the drawings, the device 10 includes an outer tubular shell 12, which serves both as a handle and a container of parts of the skin-pricker device's components for receiving and actuating a needle assembly 14 with its skin-pricking needle 16.

Other primary components are a latch and actuator mechanism 18; and with those components and others detailed herein the device 10 provides and achieves an advantageous skin-pricker 10 having the important safety specified.

The illustrated embodiment will be perhaps easiest understood by describing the components and features in terms of their function together with their construction and assembly details.

Also, preliminarily it may be mentioned that the shell 12 and its internal parts may be realistically considered as permanent, in contrast to the needle assembly 14 and its needle 16 and certain other needle-related parts which are expendible; but the expendibility is a desired factor for achievement of the safety function, i.e., of measuring against blood from a prior pricking procedure being touch by the attendant or a subsequent patient.

The expendible or disposable components, one set of which is used and then to be safely discarded in a single skin-pricking procedure, include the needle assembly 14, it being shown as having a needle 16 carried on a short cylindrical stem body 20, which is carried on a base piece 22.

The needle 16 itself as shown extends outwardly of its carrier stem 20 only that small distance to penetrate the patient's skin, but the needle's stem body 20 is sufficiently long enough to carry connector threads mentioned below.

Also, as a disposable item is a hollow tubular sheath or needle-cover sleeve 24. It is closed at one end 26 and open at the other end 28, the closed end 26 assuring against contamination, and the open end 28 open to overlie or pass over the needle 16 and the needle step 20, in operativity detailed herein.

The needle stem 20 is provided with male threads 30, and the inner wall 31 of the cover tube 24 is provided at its end 28 and female threads 32; and advantageously this releasable connectability of sheath 24 and the needle assembly 14 (by screw threads 30/32) provides that the sheath 24 may be used as a carrier of the needle assembly 14 at both the loading of the needle assembly 14 into the outer shell 12 and the subsequent removal of the needle assembly 14 therefrom after the skin-prick procedure, for safe disposal of that assembly 14, as described herein.

The uses of the cover sheath 24, and the reason for its length as being substantially longer than the needle 16 and needle stem 20, will be apparent in the description of the loading of device-cocking and latching procedures, and its great utility in safe removal of the needle assembly 14 after the skin-pricking.

The depth of the open end of the open sheath-end 28 is not critical, just as long as it will sufficiently pass over the needle's holding step 20; so it may be desired to make the sheath 24 out of hollow tubing, provided that its end 26 is closed.

Another of the disposable parts is a cover guide disk 34 having a central hole 36 having a slidable fit onto the tubular needle-sheath 24; and the disk 34 has a downwardly-extending and inwardly-extending peripheral flange 38 which releasably snaps onto a circumferential recess 40 in the shell 12's open top end 42, the hole 36 providing a guide for the sheath 24.

The above generally describes the disposable parts, although more details of their nature and function are detailed below. And hopefully the understanding of the "disposable" parts, and their relation to the "permanent" parts, will be helped at this point by an introductory summary of some of the "firing" details.

Thus turning to the non-disposable components, i.e., the outer shell 12 and its components, it will now be seen that they basically include the latch and actuator mechanism 18 mentioned above, which control (and in a sense are controlled by) a longitudinally extending control rod 44, the upper (outer) end 44x of which has an upwardly (outwardly) opening cup 46, with slots 46x, the lower (inner) end 47 of which has a firing lug 48, both the components 46 and 48 being further described below as to nature and function.

The control rod's cup 46 is of a size such that its open wall 49 will snugly yet releasably receive the needle assembly's base 22; and during loading of the disposable components by pushing a new set of those components into the shell 12, the needle base 22 enters the control rod's cup 46 (FIG. 2), and when the user continues that loading (by continuing to push downwardly on the tubular needle cover 24), the control rod 44 is pushed downwardly (inwardly) in the shell 12.

The slots 46x of the cylindrical wall 49 of the cup member 46 accommodate corners 49x of the square needle base 22, the needle assembly 14 and the shaft cup 46 (and thus also the shaft 44) being non-rotatable with respect to one another, providing for connection/disconnection explained below.

This movement of the control rod 44, as a new set of components of needle assembly 14, sleeve 24, and disk 34, is inserted through the outer-end 42 of the shell 12 in a first part of the loading or cocking procedure, is against the bias of an actuator spring 50 described below.

Such downward movement of control rod 44 correspondingly pushes the control rod lug 48 against and past the latching fingers 52, which are carried out on the inner wall of the shell 12, and are biased radially inwardly of the shell 12 and thus biased toward latching engagement with the control rod lug 48; and (FIG. 2) passing of the lug 48 past the fingers 52 achieves a latched or cocked condition of the control rod 44 and thus also the needle assembly 14, with tension having been caused to exist in the spring 50. The connection of the latching fingers 52 to the shell is shown at 53; and since so relatively small operational forces are involved, the fingers 52 in the embodiment shown achieve their movable and biasing operativity by being made of resilient or springing material.

A firing trigger 54 is slidably carried in the inner end wall 55 of the shell 12; and the trigger 54 or the latching fingers 52, or both, are slanted (56) with respect to the axis of the trigger 54's travel axially of the shell 12 such that an upward (inward) push 56x on trigger 54 by the user (FIG. 8) will fire the device by the sudden release of tension in the spring 50, as the lug 48 is released by the latching fingers 52 being pushed (as in a cam-like action) by the trigger 54 radially outwardly merely a sufficient amount such that the control rod lug 48 is no longer held by its lug-retaining engagement with the retainer lugs or latch surfaces 57 at the radially inner end of the latch-finger 52.

The spring 50 in the form shown is a tension spring ensleeved around the control rod 44, one end portion 50a being affixed to the shell 12's inner wall at connection 59 adjacent the skin-pricking end 42 of the shell 12, and the other end portion 50b of the spring 50 being affixed to the control rod 44 at connection 60 adjacent the opposite end 47 of the shell.

As to those spring connections 59 and 60, as shown, the connection 59 connects the spring to the shell 12 by being hooked into one or two support disks 62 affixed to the shell 12 adjacent the shell-ends 42 and 47, respectively. The connection 60 (as shown, FIG. 7) of the spring 50 to the control shaft 44 is shown as passing an end 63 the spring 50 through a hole 63x in the control shaft 44.

The movable support given by the disks 62 permits the axially sliding operativity of the control rod 44 within the shell 12.

In this condition of the parts, there is of course no danger of the medical technician getting touched by the patient's blood; for the needle 16 is still safely within the sheath 24, and even if there is an accidental firing from the cocked or latched (pre-firing condition (FIG. 2), the needle 16 and the needle assembly 14 cannot go to the patient, because the spring 50 is not very strong in comparison to the retention of the cap or disk 34 by the retainer components 38 and 40.

In the device-loading procedure, the medical technician will have brought the sheath 24 with the needle assembly 14 and cover disk 34 carried by the sheath 24 over to the recipient shell 12, and then have pushed (downwardly as the parts are shown) on the sheath 24 to push the needle base 22 into the open end 42 of the shell 12, until the needle base 22 is received in the control rod's cup 46.

The cup walls 49 and the needle base 22 are sized to accommodate that assembly (22/49), and are relatively non-rotatable as mentioned above.

To achieve the latched condition (FIG. 2) the technician will have pushed on the carrier sheath 24, that pushing force acting through the cup 46 and control rod 44 to force the control rod abutment 48 to a latched (downward as here shown) positioned by engaging the cam walls 64 of the latch fingers 52 until the rod lug 48 is latched behind the latch finger walls 57. The cam walls 64 are the walls of fingers 52 facing the open end 42 of the shell 12.

This pushing on the sheath 24 stretches the spring 50, biasing the control rod 44's cup 46 and the needle-base 22 and needle 16 into condition for the skin-pricking.

Next, the technician pushes (downwardly as here shown) the sheath's disk 34 towards the open end 42 of the shell 12 until the disk 34's flange 38 snaps into the shell 12's end-groove or recess 40 (FIG. 2).

Now that the needle assembly 14 is resting in the shell 12 by the needle assembly's base 22 seated in the rod-cup 46, and the disk 34 is retained on the shell 12 by the hold of disk-flange 38 by the shell's annular groove 40, and with the relative non-rotatability of the base 22 and the walls 49 of the cup 46 holding the base 22 from rotation, the technician unscrews the sheath 24 from the needle's item 20; and, with the disk 34 being held (38/40) on the shell 12, the user pulls the sheath 24 outwardly of the disk 34 and shell 12, and puts the sheath 24 aside for later use detailed herein.

Still there is no danger to the technician.

(For the steps of the screwing and unscrewing of the threads 30/32, the inventors believe that the actuator shaft and its receiver cup 46 will be held sufficiently non-rotatable to the shell 12 by torsional resistance of the spring 50, particularly by its attachments 59 and 60, respectively, to the shell 12 and the shaft 44 without need of any twist-blocker lug and longitudinal slot, which could be provided on the shaft 44 or cup 46, cooperative with a complementary component on the inner wall of the shell 12 or carried by one or both of the support disks 62.)

It is to be noted that the various components are sized relatively to one another that in this latched or loaded condition, the assembled device 10 is now ready for "firing", i.e., causing the needle 16 to quickly extend and then quickly retract, as the device is held with the disk 34's outer wall 66 pressing against a patient's finger in the finger-pricking task.

Further, the parts are so related such as to provide (FIG. 8 that a firing, by a push on the trigger 54 to cause the latch-fingers 52 to release the control rod abutment 48, will permit the stretched spring 50 to act on the control rod 44 (by the spring 50's connection thereto at 60) to quickly force (arrows 65) the needle 16 outwardly (upwardly here) of the disk 34's outer wall 66, a small distance desired for the finger-pricking effect.

More particularly as to the spring 50, it is of a slightly open-coil nature; and this, as well as the nature and size relation of the parts, provides that when the device is fired, the spring 50 will permit the inertia of the control rod 44 to cause the outward (here upward) travel of the needle assembly 14 to be such as to not only carry the needle 16 to an outer position although still within (here under) the location of the outer wall 66 of the disk 34, as being the position when the spring 50 is wholly "at rest", i.e., not in either tension or compression, but also the outward (here upward) travel of the needle assembly 14 will, by that inertia effect, have (FIG. 8) travelled outwardly (here upwardly) of the disk's outer wall 66 the desired extra although small distance outwardly (here upwardly) for the finger-pricking operativity.

Then, after the finger-pricking has been achieved by the user having held the disk wall 66 against the patient's finger during firing, the spring 50's compression (even though slight) as caused by the overtravel or inertia effect, will cause the spring 50 to instantly relieve its compressive stress, with a corresponding inner (here downward) travel of the rod 44, rod-cup 46 and needle assembly 14, to an at-rest condition in which the needle 16 is fully and safely inwardly in the hole 36 of the disk 34 and especially inwardly of the disk 34's outer wall 66.

Still no blood from the skin-pricking procedure gets on the medical technician.

Next, the technician again picks up the sheath 34, and inserts the open end 28 of the sheath 24 through the disk-hole 36 into an ensleevement of the sheath's open end 28 over the needle 16 and needle-stem 20 until the sheath threads 32 engage the needle-stem 20's threads 30, whereupon a twisting effort as to the sheath 24, with the needle base 22 and rod-cup 46 being not relatively rotatable, makes ready a screw-threaded re-capturing of the needle assembly 14, for removal of the needle assembly 14 from the rod-cup 46, and release of the non-assembled needle assembly 14 and disk 34 from the holder shell 12, by pulling outwardly (here upwardly) on the sheath 24.

And still there is safety from any blood from the patient.

Then that outward (here upward) pulling on the sheath 24 causes the outer (here upper) wall 68 of the needle base 22 to engage the inner (here lower) wall 70 of the disk 34, and further-continued outward (here upward) pulling on the sheath 24 causes the disk-flange 38 (and thus the entire disk 34) to be released from the annular shell recess 40; and then the assembly of sheath 24 and needle assembly 14, and disk 34 are discarded.

Full safety from the needle 16 and the patient's blood is thus seen to continue through the disassembly procedure; and further, all the components which seem most likely to have any blood (i.e., the needle 16, the needle's holder stem 20 and its threads 30, and the outer (here top) wall 68 of the needle base 22) are all quite wholly and quite safely positioned inwardly of the assembly (24, 14, 34) being discarded.

Additional safety is provided by the two axially-spaced supports disks 62 in the shell 12, each having a central hole 74 through which the control rod passes. These supporting disks 62 provide a centering of the control rod 44 and thus also of its reception cup 46, which permits easy co-axial registry during the step of re-capturing the needle assembly 14 after the finger-pricking, a feature which helps avoid any disadvantage of the technician not being able to see visually the proper registry or ensleevement of the open sheath-end 28 and needle stem 20 as needed for engagement of their respective threads 32 and 30.

Supplementary description in operational or use review (Let it be assumed for description purposes that the user is starting will all new components.)

An expendible needle assembly 14 (new) would have its sheath 24 carrying a needle assembly 14 by the sheath 24's threads 32 being threaded onto the needle stem 20's threads 30, with a disk 34 carried on the sheath 24. The needle 16 itself is not exposed. The carry of the disk 34 on the sheath 24 is slidable, by a slight difference in the sizes of sheath 24 and the cap-hole 36.

Consider now the "permanent" components, i.e., the shell 12 and the components it carries.

The spring 50 would be in an at-rest condition in the shell 12; and the control stem or rod 44 is in a position as shown in FIG. 1 in which it is not cocked (the control rod end lug 48 is not behind the latch finger retainer walls 57), and the trigger 54 is being held in its outer position (FIG. 1) by the radially inward bias of the latch fingers 52; for just as the trigger 54 forces the latch fingers 52 radially outwardly during firing, so do the latch fingers 52 force the trigger 54 to its outer (FIG. 1) position while in an at-rest condition.

The non-firing position of the trigger 54 is an outer position, as shown in FIG. 1, i.e., with the trigger 54's actuation head 58 extending outwardly of the shell 12 at its end portion 55, providing for manual pressing by the user to cause the firing movement of the rod 44; and that outward extension of the trigger's actuation head 58 is through a hole 58a in the transverse end wall 58b of the shell 12/55.

During this non-firing or at-rest condition of the trigger 54, it is held in that outer (FIG. 1) position by its outward travel being blocked by the engagement of a trigger body shoulder 58c abutting the portion of the shell's transverse lip or end wall 58b which is adjacent the hole 58a.

First, the user brings the needle assembly (14, 24, and 34) to the shell 12, the shell 12 then being in the at-rest position (FIG. 1), and then, holding them by grasping merely the sheath 24, the user inserts the needle base 22 into the open end 42 of the shell 12, far enough to seat the needle base 22 in the rod-cup or receiver 46.

Then, with the needle assembly 14 being held against rotation by the rotationally-fixed nature of base 22 and cup 46, the user continues to push on the sheath 24 to move the rod 44 from the unlatched position (FIG. 1) to the latched position (FIG. 2) of the rod-lug 48, and the user pushes the disk-cap 34 onto the open end 42 of the shell 12 hard enough to engage the abutment walls 38/40; and then an unscrewing of the sheath 24 brings it out of the cap-hole 36 for later use.

The parts are now in the position of FIG. 2, except only that the sheath 24 would be then off the assembly.

After the sheath 24 is removed, the at-rest position of the needle 16 is still below that cap face 66.

Then, in firing (FIG. 8) the needle 16 moves only a small distance needed for the skin-pricking procedure; and then the rebound characteristic of the spring 50 instantly and automatically brings the needle 16 back to its position (FIG. 9) safely within the cap 34.

Then, without any touching of the needle 16 or the cap 34 at all, the technician re-enters the sheath 24 into the cap hole 36, ensleeving the needle 16 and needle stem 20, and by twisting the sheath re-engages the threads 30/32, and by pulling on the sheath 24 withdraws the discard assembly 16/14/24/34 away from the shell 12, shell 12 being then ready to re-use, but with the discard assembly safely carried to a waste receptacle, a carrying task requiring touching only the sheath, and with all parts of the needle assembly which had been exposed to the skin-pricking procedure automatically forced into the recess 28/31 of the sheath 24.

Thus, it is seen that the device and procedure are very safe, at each step, and yet it is easy to use.

Conclusion

It is thus seen that a skin-pricker device, especially as provided and used according to the inventive concepts herein set forth, provides novel concepts of a desirable and advantageous device, yielding the advantages of a safely-usable device having advantageous safety and ease-of-use details and features, which, in overall combination, are conceptually different and provide a novel device different from the prior art even though various objects embodying certain of the mechanical details as a basic capability have of course been known for years; yet significantly this particular combination, even considered as including or building on prior art concepts, has not been suggested by the prior art, this achievement being a substantial and advantageous departure from prior art, all this even though the prior art has made attempts at improvement and variations as to skin-pricking devices and procedures for many years, and surely throughout an untold number of skin-pricking procedures, and with most every person of the modern world having received a skin-pricking procedure. And particularly is the overall difference from the prior art significant when the non-obviousness is viewed by a consideration of the subject matter as a whole, as integrally incorporating a combination of features as different from the prior art, in contrast to merely those details of novelty themselves, and further in view of the prior art teaching away from the particular and interrelated concepts and features of the present invention.

In summary so to the nature of these advantageous concepts, their inventiveness is shown by novel features of concept and construction shown here, in novel and advantagous combination, not only being different from all the prior art known, but because the achievement is not what is or has been suggested to those of ordinary skill in the art, especially realistically considering this as comprising components which individually are similar in nature to that is well known to makers and users of manually operable devices, including devices for medical use, for many years. No prior art has suggested the modifications of any prior art to achieve the novel concepts here achieved, with the various features providing their own functions in the overall combination; and this is particularly significant since medical devices are in a very commercial field of art, and because skin-pricking devices are objects whose safety characteristics are recognized to be quite vital.

Accordingly, it will thus be seen from the foregoing description of the invention according to this illustrative embodiment, considered with the accompanying drawings, that the present invention provides new and useful concepts of a novel and advantageous skin-pricking device, having and yielding desired advantages and characteristics in formation and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment, or form or arrangement of parts herein described or shown.

We claim:

1. A skin pricker device kit comprising, in combination:

a hollow tubular shell;

a control shaft;

support means supporting the control shaft within the shell but permitting it to move axially of the shell;

the shell having a skin-pricking end, and the shell extending from the skin-pricking end providing a handle by which the person administering the skin-pricking procedure may carry the shell and administer the skin-pricking procedure;

first spring means carried by the shell, and biasing the control shaft toward the skin-pricking end of the shell;

a needle having a sharp end for pricking the skin of the person whose skin is to be pricked and an opposite end for receiving support for the needle;

a support base which supportively carries the needle;

the control shaft having at its skin-pricking end a receiver of the needle's support base;

the receiver and the support base being formed to provide them to be non-rotatable with respect to one another;

there being second spring means biasing the control shaft opposite from the bias imposed by the first spring means, and the second spring means being operable, after the first spring means has caused the control shaft to move to force the needle the axial distance needed for the skin-pricking procedure, to cause the control shaft to move the needle oppositely to its skin-pricking movement;

and manually operable control means for controlling whether the first spring means is in a stressed or unstressed condition;

in a combination in which the needle support base and the needle are connected by a needle stem, and in which there is provided a hollow carrier sleeve closed at one end but open at its other end, the said other end having female screw threads, and the sleeve's open end having a recess in which the needle and the needle's stem are receivable;

the needle's support base having male screw threads which are screw-threadedly engageable with the female screw threads of the carrier sleeve;

and in which there is provided a cap body having an opening, the opening accommodating the reception therethrough of the carrier sleeve;

the cap body and the shell, at the skin-pricking end of the shell, having cooperative retention means by which the cap body provides an abutment blocking the needle assembly from moving outwardly of the shell except as the carrier sleeve pulls the needle's support base by force transmitted through the said threaded engagement of the threads of the sleeve and support base, which can occur only if the needle and needle stem are received in the carrier sleeve.

2. The invention as set forth in claim 1, in which the first spring means and the second spring means are provided by a single spring, that spring being a tension spring of open-coil nature when unstressed, and providing the said operativity of moving the control shaft and needle in a first direction for enabling the needle to move to its skin-pricking position but also the operativity of moving the control shaft and needle then in the other direction which withdraws the control shaft and needle from the skin-pricking position of the needle.

3. The invention as set forth in claim 1, in which there are provided latch means which releasably retain the control shaft in a position in which the needle is in a retracted position away from its skin-pricking position,
   the support means of the control shaft providing that the control shaft is movable into and between three positions, those positions being: (a) a skin-pricking position in which it is pushing the receiver and the needle base such that the needle's skin-pricking end is outwardly of the shell, in a skin-pricking position; and (b) the retracted position specified above, and in which the first spring means is latched under tension biasing the control shaft to its skin-pricking position; and (c) an intermediate position in which the first spring means is unstressed; the positions "(b)" and "(c)" being such that the skin-piercing end of the needle is in a retracted position within the skin-pricking end of the shell.

4. A skin pricker device kit comprising, in combination:
   a hollow tubular shell;
   a longitudinally extending control member;
   support means supporting the longitudinally extending control member within the shell but permitting it to move axially of the shell;
   the shell having a skin-pricking end, and the shell extending from the skin-pricking end providing a handle by which the person administering the skin-pricking procedure may carry the shell and administer the skin-pricking procedure;
   first spring means carried by the shell, and biasing the longitudinally extending control member toward the skin-pricking end of the shell;
   a needle having a sharp end for pricking the skin of the person whose skin is to be pricked, and the needle also having a support portion spaced from the needle's sharp end for receiving support for the needle;
   a support base connected to said support portion, and which supportively carries the needle;
   the longitudinally extending control member having at its skin-pricking end a receiver of the needle's support base;
   the receiver and the support base being formed to provide them to be non-rotatable with respect to one another;
   there being second spring means biasing the longitudinally extending control member oppositely from the bias imposed by the first spring means, and the second spring means being operable, after the first spring means has caused the longitudinally extending control member to move to force the needle the axial distance needed for the skin-pricking procedure, to cause the longitudinally extending control member to move the needle oppositely to its skin-pricking movement;
   and manually operable control means for controlling whether the first spring means is in a stressed or unstressed condition;
   in which the needle support base and the needle are connected by a needle stem, and in which there is provided a hollow carrier sleeve closed at one end but open at its other end, the said other end having female screw threads, and the sleeve's open end having a recess in which the needle and the needle's stem are receivable;
   the needle's support base having male screw threads which are screw-threadedly engageable with the female screw threads of the carrier sleeve;
   and in which there is provided a cap body having an opening, the opening accommodating the reception therethrough of the carrier sleeve;
   the cap body and the shell, at the skin-pricking end of the shell, having cooperative retention means by which the cap body provides an abutment blocking the needle assembly from moving outwardly of the shell except as the carrier sleeve pulls the needle's support base by force transmitted through the said threaded engagement of the threads of the sleeve and support base, which can occur only if the needle and needle step are received in the carrier sleeve.

* * * * *